United States Patent [19]

Stickney et al.

[11] 4,005,204
[45] Jan. 25, 1977

[54] TREATMENT OF NEOPLASMS IN THE BRAIN WITH DIAMINO DICHLOROALKYL PYRIMIDINE

[75] Inventors: Dwight R. Stickney; William S. Simmons; Charles A. Nichol; George H. Hitchings, all of Durham; Gertrude B. Elion, Chapel Hill, all of N.C.

[73] Assignee: Burroughs Wellcome Co., Triangle Park, N.C.

[22] Filed: Feb. 12, 1975

[21] Appl. No.: 549,453

Related U.S. Application Data

[62] Division of Ser. No. 344,179, March 23, 1973, abandoned.

[52] U.S. Cl. .................................. 424/251
[51] Int. Cl.² ................................ A61K 31/505
[58] Field of Search .......................... 424/251

[56] References Cited

OTHER PUBLICATIONS

Murphy et al. J. Clin. Invest. vol. 33 (1954) pp. 1388 et. seq.
Geils et al—Blood vol. 38 No. 2 (1971) pp. 131–137.

*Primary Examiner*—Sam Rosen
*Attorney, Agent, or Firm*—Donald Brown

[57] ABSTRACT

Method and pharmaceutical preparations for treating meningeal leukemia, CNS lymphoma and neoplasms in the brain which comprises treating an infected mammal such as a human with a dose of an effective treatment amount of a compound of Formula I

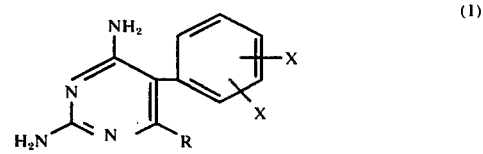

where R is a straight or branched chain lower alkyl of 1 to 4 carbon atoms, and X is a halogen atom (fluorine, chlorine, bromine or iodine) and pharmaceutically acceptable salts thereof.

Preferred compounds for treatment of the aforementioned diseases are 2,4-diamino-5-(3',4'-dichlorophenyl)-6-methylpyrimidine and 2,4-diamino-5-(3',4'-dichlorophenyl)-6-ethylpyrimidine.

6 Claims, No Drawings

TREATMENT OF NEOPLASMS IN THE BRAIN WITH DIAMINO DICHLOROALKYL PYRIMIDINE

This is a division of application Ser. No. 344,179, filed on Mar. 23, 1973, now abandoned.

BACKGROUND OF THE DISCLOSURE

This invention relates to a method of treating meningeal leukemia and CNS lymphoma and neoplasms in the brain in man and pharmaceutical preparations suitable for such use.

More effective antileukemic therapy and consequent longer survival has the unfortunate consort of an increase in the number of human patients developing meningeal leukemia. This is a more common occurrence in children than adults; 50 to 85 percent of the children in whom acute lymphoblastic leukemia has been controlled by chemotherapy have developed leukemic meningitis. since most drugs used in the treatment of acute leukemia do not pass the blood-brain barrier, the central nervous system may serve as a sanctuary for leukemic cells and may act as a nidus for systemic relapse.

It has been previously demonstrated that 2,4-diamino-5-(3',4'-dichlorophenyl)-6-methylpyrimidine (DDMP) and, 2,4-diamino-5-(3',4'-dichlorophenyl)-6-ethylpyrimidine (DDEP) have an inhibitory activity against a variety of cancerous conditions. For example, antitumor activities against mouse Sarcoma 180 [Clarke, etal., *Cancer Research*, 12, 255(1952)] and against mouse leukemia have been reported in Cancer Research, Burchenal et al., *Cancer Research*, 12 251,(1952). More recently the treatment of meningeal leukemia with pyrimethamine [2,4-diamino-5-(4'λ chlorophenyl)-6-ethylpyrimidine], has been reported [Geils, etal. *Blood*, 38, 131 (1971)].

It is also known that pyrimethamine readily crosses the blood-brain barrier and indeed apparently has easy access to all body compartments and cells [Hitchings, Discussion of paper by Bertino, etal., *Fed. Proc.* 26, 896 (1967)]. This property assumes great significance in the treatment of leukemia as well as other cancerous conditions involving metastasis.

For example, an effective anti-leukemic agent which could not pass the blood-brain barrier would not be effective against meningeal leukemia, a condition in which leukemic cell infiltration of the arachnoid membrane has occurred. Methotrexate is known to be effective against leukemia and is also known to be unable to cross the blood-brain barrier. Thus, in order for methotrexate to be effectively used against meningeal leukemia it must be administered intrathecally [Geils et.al., *Blood*, 38, 131 (1971)].

Murphy and co-workers [J. Clin. Invest., 33, 1388 (1954)] reported clinical studies of the therapeutic activity of DDMP against leukemia in children and adults as well as against several other cancerous conditions. Significant toxic manifestations characteristic of antagonists of the folic acid system were observed.

DESCRIPTION OF THE DISCLOSURE

This invention relates to a method of treating meningeal leukemia and central nervous system (CNS) lymphoma and in general neoplasms in the brain in mammals such as man and pharmaceutical preparations for use therefore.

In particular compounds of the Formula I

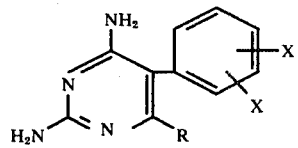

or pharmaceutically acceptable salts thereof where R is lower alkyl of 1 to 4 carbon atoms (straight or branched chain) and X is a halogen atom (fluorine, chlorine, bromine or iodine) are useful for treating meningeal leukemia and CNS lymphoma and in general neoplasms in the brain and as the active medicinal ingredient in a pharmaceutical preparation suitable for treating the above mentioned diseases.

Within the scope of Formula I compounds of Formula II

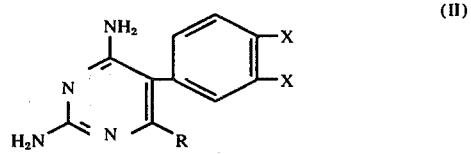

where X and R are defined as above, and pharmaceutically acceptable salts thereof are preferred.

Compounds of outstanding interest for the treatment of the aforementioned diseases and in pharmaceutical preparations therefore are 2,4-diamino-5-(3',4'-dichlorophenyl)-6-methylpyrimidine (DDMP) and 2,4-diamino-5-(3',4'-dichlorophenyl)-6-ethylpyrimidine (DDEP) and pharmaceutically acceptable salts thereof.

The compounds of Formula I, II and the compounds of outstanding interest may be prepared according to U.S. Pat. No. 2,594,309. Included in the examples of this patent are the synthesis of DDMP and DDEP as well as other compounds encompassed by Formula I.

Salts which are especially preferred for therapeutic use are salts of pharmaceutically acceptable carboxylic acids such as lactic, acetic, malic as well as the salts of pharmaceutically acceptable mineral acids although it should be understood that the activity of any salt administered or used medicinally resides in the base (active ingredient).

Most importantly, it has now been found that these compounds of Formula I, II including DDMP and DDEP readily penetrate the various cells and compartments of the human body and that in particular these compounds cross the blood-brain barrier and concentrate in the brain.

Unexpectedly these compounds and in particular DDMP and DDEP were found to be significantly more favorably positioned between brain and blood then pyrimethamine mentioned previously. For example, two hours after dosing rats at 10 mg/kg the brain/plasma concentration ratio of DDMP was 12 while that of pyrimethamine administered at the same dosage was 2.6.

Experiments have also shown that the compounds of Formulas I, II including DDMP and DDEP have surprisingly long half-lives. The plasma half-life of pyrimethamine has been determined to be about 92 hours, a rather long half-life for a pharmaceutical whereas the half-life of DDMP has now been found to be, remarkably, in excess of 300 hours. Thus acceptable blood levels of DDMP as well as the other compounds useful herein can be maintained for treatment of meningeal leukemia CNS lymphoma and neoplasms in the brain with significantly less frequent dosing. In addition the teachings of this invention disclose how to successfully use the compounds in treating patients without causing inacceptable toxicity due to overdosing.

The compounds useful in this invention as set forth above are internally administered and may conveniently be administered orally or parenterally. For oral administration the compounds may be presented in unit dosage form such as tablets, capsules, cachets or ampules, each containing an effective non-toxic antimeningeal leukemia or anti-CNS lymphoma treatment amount of the compounds of Formula I, II, DDMP or DDEP (the active ingredients) and a pharmaceutically acceptable carrier therefore.

For parenteral administration the active ingredient may be presented as part of a solution or in suspension in an aqueous, non-aqueous or emulified liquid, each containing an effective non-toxic anti-meningeal leukemia or anti-CNS lymphoma treatment amount of the active ingredient and a pharmaceutically acceptable carrier therefore.

The pharmaceutical formulations of this invention may be made by any of the methods of pharmacy and may include one or more of the following accessory ingredients: diluents, solutes, buffers, flavoring, binding, dispensing, surf-active, thickening, lubricating and coating materials, preservatives, antioxidants, bacteriostats, and many other acceptable excipients.

For treatment of meningeal leukemia in man (humans being used interchangeable with man herein) a preferred dosage (as base) of the compounds of Formula I, II, DDMP or DDEP, is about 1 to 5 mg/kg of bodyweight (man) initially, followed by 0.2 to 5 mg/kg of bodyweight (man) every 4 days. The most preferred dosage would initially be 1 to 2 mg/kg of human bodyweight and .2 to 1 mg/kg of human bodyweight every four (4) days.

The compounds of Formula I, II, DDMP or DDEP (the active ingredient) for the treatment of meningeal leukemia are preferably provided in a pharmaceutical preparation containing per dosage unit 1 to 100 milligrams (base) of active ingredient.

For treatment of CNS lymphoma in man (humans) a preferred dosage (as base) of the compounds of Formula I, II, DDMP or DDEP is about 1 to 5 mg/kg of bodyweight (man) initially followed by 0.2 to 5 mg/kg of bodyweight (man) every 4 days. The most preferred dosage would initially be 1 to 2 mg/kg of human bodyweight and 0.2 to 1 mg/kg of human bodyweight every 4 days.

The compounds of Formula I, II, DDMP or DDEP (the active ingredient) for the treatment of CNS lymphoma are preferably provided in a pharmaceutical preparation containing per dosage unit 1 to 100 milligrams (base) of active ingredient.

It is known that the hematological activity of DDMP can be prevented or reduced by the simultaneous administration of Leucovorin (5-formyl-5,6,7,8-tetrahydrofolic acid). Consequently, brain levels of DDMP may be safely raised by increasing the dosage of DDMP together with a simultaneous administration of Leucovorin.

For the treatment of neoplasms lodged in the brain, the compounds of Formula I, II including DDMP and DDEP are administered in the same dosage and regime as in treating CNS lymphoma above and pharmaceutical formulations therefore are in the same unit dosage as mentioned above.

As a further aspect of this invention there is provided a new and improved method of treating patients (man) undergoing treatment with drugs (as used herein drugs includes radiation, chemotherapeutic drugs and immunological agents e.g., vaccines) for other types of neoplasms or leukemia in other parts of the body so as to treat or prevent meningeal leukemia, CNS lymphoma and neoplasms in the brain.

In particular this aspect of the invention comprises the administration of the chemotherapeutic compound of Formula I, II DDMP or DDEP before, during or after i.e., in conjunction with administration of the aforementioned drugs for combatting neoplasms or leukemia in the patient (man).

The dose regime and amounts of the chemotherapeutic compound of Formula I, II, DDMP or DDEP are the same as given above in treating CNS lymphoma and the pharmaceutical formulations therefore are in the same unit dosage as mentioned above.

For example, the compounds of Formula I, II, DDMP or DDEP may be administered in conjunction with antineoplastic and antileukemia agents such as methotrexate, a known antineoplastic agent 6-mercaptopurine a known anti-leukemia agent, 6-thioguanine, a known anti-leukemia agent, 1,4-dimethanesulfonoxybutane a known anti-leukemia agent, chloroambucil, a known anti-leukemia and anti-lymphoma agent, vincristine sulfate, a known anti-leukemia agent, cytarabine, a known anti-leukemia agent, cyclophosphamide a known anti-leukemia agent.

The dosages for administration for the above mentioned chematherapeutic agents are known and may be found by consulting the Physicians Desk Reference, 1973, or the packaging inserts provided by the manufacturer. For example, methotrexate may be administered orally at 15 to 30 mg daily for 5 days. 6-mercaptopurine may for example be given at a dose of 50 mg. for a child of 5 years old.

Accordingly this invention provides a new and unexpected method and preparation for treating patients with the compounds of Formula I, II, DDMP or DDEP, in a manner such that through intermittant dosing unacceptable toxicity is reduced (because of the unexpectedly long half-life of these compounds), while providing sufficient compound in the amounts and the place where needed to effectively treat the aforementioned diseases.

This invention is also useful in the same mg/kg dosages as prescribed above for the treatment of humans for treating mammals such as animals of the species of mice, rats, dogs etc. (mammals obviously includes humans) which may be afflicted with such diseases as previously mentioned above (e.g., neoplasms in the brain) or in which the disease has been transplanted.

As used herein a non-toxic amount or dose means an acceptable amount or dose which although it may cause some toxic symptoms is not fatal to the patient.

The following Examples illustrate but should not be construed as limiting this invention:

EXAMPLE 1

2.5 mg. Tablet

The active ingredient DDMP (50.0 g.), dried potato starch (280.0 g.), pregelatimized corn starch (54.0 g.) and lactose (2462.0 g.) were hand-screened thru 70 mesh sieves and then transferred into a planetary mixer and mixed for 15 minutes at 28 rpm. Water (550 g.) was added and wet-mixed with the blended powders for 5 minutes at 28 rpm. Granulation was carried out by passing the material thru a 16 mesh screen, and the granulated material was subsequently dried in a tray dryer at 43° C for 16 hours to a moisture content of 1.1%. The dried material was sifted thru a 20 mesh screen, mixed with magnesium stearate (70 mesh 14.0 g.) and the mixture compressed into tablets in a rotary tablet press fitted with 7.4 diameter punches and dies, each tablet weighing 143 mg. and containing 2.5 mg. of DDMP.

EXAMPLE 2

10 mg. Tablet

The general procedure of Example 2 was followed using the following ingredients:

| | |
|---|---|
| DDMP | 200.0 g. |
| Lactose | 2312.0 |
| Potato starch, dried | 280.0 |
| Pregelatimized starch | 54.0 |
| Magnesium stearate | 14.0 |

The tablets, compressed from this composition each weighed 143 mg. and contained 10.0 mg. of DDMP.

EXAMPLE 3

The general procedure of Example 1 was followed except that DDEP was used as the active ingredient.

EXAMPLE 4

The general procedure of Example 2 was followed except that DDEP was used as the active ingredient.

EXAMPLE 5

| Ingredients | |
|---|---|
| DDMP | .5 grams |
| Lactic acid | .30 grams |
| $H_2O$ q.s. | 100 ml |

DDMP is stirred in hot water (about 90 ml) at 70° to 80° C for five minutes and lactic acid is then added, the mixture is then heated to 98° C and then cooled to room temperature and water is added to make up 100 ml volume. Product is then filtered. This gives an injectable product with 5 mg/ml. DDMP.

EXAMPLE 6

Same as Example 5 with DDEP being used to form an injectable solution.

We claim:

1. A method of treating neoplasms in the brain of a mammal which comprises administering to the infected mammal a non-toxic anti-neoplastic effective amount of the compound 2,4-diamino-5-(3',4', dichlorophenyl)-6-methylpyrimidine or a pharmaceutically acceptable salt thereof.

2. The method of claim 1 in which the compound is administered each time a few days apart from the previous administration thereof.

3. The method of claim 1 in which the mammal is a human.

4. A method of treating neoplasms in the brain of a mammal which comprises administering to the infected mammal a non-toxic, anti-neoplastic effective amount of the compound 2,4-diamino-5-(3',4'-dichlorophenyl)-6-ethyl pyrimidine or a pharmaceutically acceptable salt thereof.

5. The method of claim 4 in which the compound is administered each time a few days apart from the previous administration thereof.

6. The method of claim 4 in which the mammal is a human.

* * * * *